United States Patent [19]

Sale et al.

[11] 4,075,342

[45] Feb. 21, 1978

[54] ANTIREPRODUCTIVE IMIDAZO[2,1-a]ISOQUINOLINE COMPOUNDS

[75] Inventors: Amedeo Omodei Sale, Pavia; Emilio Toia, Milan; Giulio Galliani, Milan; Leonard J. Lerner, Milan, all of Italy

[73] Assignee: Gruppo Lepetit, S.p.A., Milan, Italy

[21] Appl. No.: 629,339

[22] Filed: Nov. 6, 1975

[30] Foreign Application Priority Data

Nov. 23, 1974 United Kingdom .............. 50855/74

[51] Int. Cl.² .................... C07D 471/04; A61K 31/47
[52] U.S. Cl. .............................. 424/258; 260/283 S; 260/283 CN; 260/286 R; 260/287 CF; 260/288 D; 260/288 CF; 260/289 R; 260/326.1; 424/273 R; 424/273 P; 542/416; 542/420; 548/323; 548/324; 548/326; 548/369; 548/378
[58] Field of Search ................. 260/288 CF, 287 CF; 424/258

[56] References Cited

U.S. PATENT DOCUMENTS 3,652,570  3/1972  Gittos et al. ............... 260/288 CF
3,887,566  6/1975  Rodway et al. ............. 260/288 CF

OTHER PUBLICATIONS

Krohnke et al., Ber., vol. 95, pp. 1128–1137, (1962).
Habermaly et al., Chem. Ber., vol. 108, pp. 984–985, (1975).
Kroehnke et al., Chem. Abs., vol. 57:5889, (1962).
Cookson et al., Chem. Abs., 82:140016c, (1974).

Primary Examiner—Donald G. Daus
Assistant Examiner—Mary Vaughn
Attorney, Agent, or Firm—Daniel D. L. DeJoseph

[57] ABSTRACT

Novel tricyclic compounds containing two ring notrogen atoms and represented by the following formula I

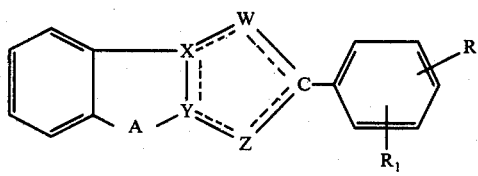

wherein:

A is one of the groups —CH₂—; —CH=CH—; and —CH₂—CH₂—;

R is hydrogen, lower alkyl, lower alkoxy, lower alkenyloxy, lower alkynyloxy, cyclo(C₃₋₆alkyl)oxy, hydroxy, benzyloxy, halo, sulfamoyl, cyano, trifluoromethyl or nitro; R₁ is hydrogen, lower alkoxy or halo; or R and R₁ taken together are methylenedioxy; the sequence

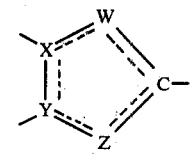

is one of the following moieties:

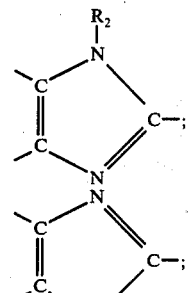

a)

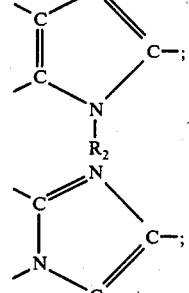

b)

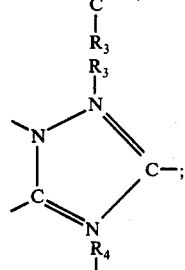

c)

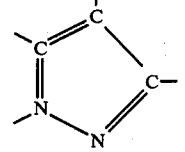

d)

e)

wherein R₂ is hydrogen or lower alkyl; R₃ is hydrogen or lower alkyl; R₄ is hydrogen, methyl, carboxy, carbo(-lower alkoxy), carbamyl, mono- or di-(lower alkyl) carbamyl or hydroxymethyl; provided that when the sequence

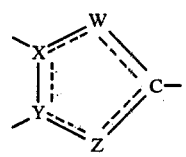

is one of the moieties a) and b) wherein R₂ is hydrogen or lower alkyl, A is not —CH=CH—; when the sequence

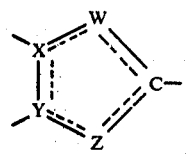
is one of the moieties (a) and (b) wherein $R_2$ is hydrogen, A is not —$CH_2$—; and when the sequence
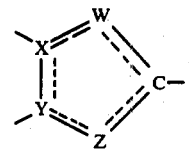
is one of the moieties (c) and (d) wherein $R_3$ is hydrogen and when both R and $R_1$ are hydrogen, A is not —CH=CH—; and the salts thereof with a non-toxic pharmaceutically-acceptable acid. The compounds of the invention have antireproductive activity.
6 Claims, No Drawings

ANTIREPRODUCTIVE IMIDAZO[2,1-a]ISOQUINOLINE COMPOUNDS

SUMMARY OF THE INVENTION

This invention relates to novel tricyclic compounds containing two ring nitrogen atoms represented by the following formula I

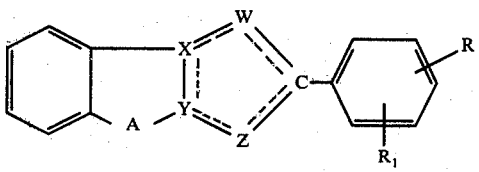

wherein:

A represents one of the groups —CH$_2$—; —CH═CH—; and —CH$_2$—CH$_2$—;

R represents one of the groups hydrogen, lower alkyl, lower alkoxy, lower alkenyloxy, lower alkynyloxy, cyclo(C$_{3-6}$alkyl)oxy, hydroxy, benzyloxy, sulfamoyl, cyano, fluoro, chloro, bromo, iodo, trifluoromethyl or nitro;

R$_1$ represents one of the groups hydrogen, lower alkoxy, fluoro, chloro and bromo, or R and R$_1$ taken together represent methylenedioxy; the sequence

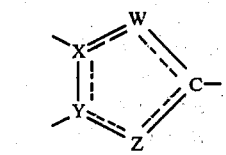

represents one of the following moieties:

a) 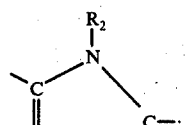

b) 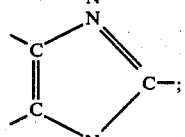

c) 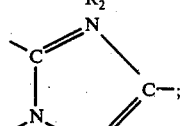

d) 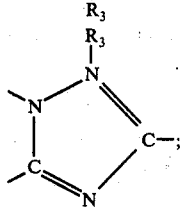

e) 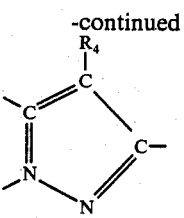

wherein R$_2$ is hydrogen or lower alkyl, R$_3$ is hydrogen or lower alkyl; R$_4$ is hydrogen, methyl, carboxy, carbo-(lower alkoxy), carbamyl, mono- or di-(lower alkyl)-carbamyl or hydroxymethyl; provided that:

when the sequence

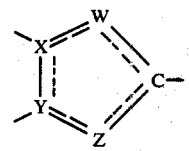

represents one of the moieties (a) and (b) wherein R$_2$ is hydrogen or lower alkyl, A is not —CH═CH—;

when the sequence

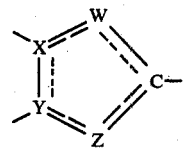

represents one of the moieties (a) and (b) wherein R$_2$ is hydrogen, A is not —CH$_2$—;

and when the sequence

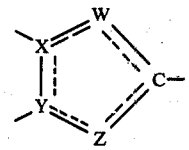

represents one of the moieties (c) and (d) wherein R$_3$ is hydrogen and when both R and R$_1$ are hydrogen, A is not —CH═CH—; and the salts thereof with a non-toxic pharmaceutically-acceptable acid.

The compounds of the invention have antireproductive activity. In particular, they show a remarkable post-coital-post implantation anti-fertility activity.

This invention also provides a method for inhibiting reproduction in mammals by administering said compounds.

This invention also provides compositions for inhibiting fertility in mammals which contain said compounds.

In the specification and claims, the term "lower alkyl" and the moiety "lower alkyl" identify a branched or linear alkyl radical containing from 1 to 5 carbon atoms, e.g., one of methyl, ethyl, propyl, isopropyl, butyl, isobutyl, tert-butyl, pentyl and neopentyl.

The term "lower alkoxy" designates a branched or linear 1 to 5 carbon atom alkoxy group, e.g., one of methoxy, ethoxy, propoxy, isopropoxy, isobutoxy, tert-butoxy, pentyloxy, isoamyloxy, 2-methylbutoxy and neopentyloxy.

The term "lower alkenyloxy" identifies a branched or linear 3 to 5 carbon atom alkenyloxy group, e.g., one of allyloxy, 2butenyloxy, 1-methyl-2-propenyloxy, 1,1-dimethyl-2-propenyloxy, 3-methyl-2-butenyloxy, 2-pentenyloxy, 3-pentenyloxy and 4-pentenyloxy.

The term "lower alkynyloxy" identifies a branched or linear 3 to 5 carbon atom alkynyloxy group, e.g., one of propargyloxy, 2-butynyloxy, 1-methyl-2-propynyloxy, 1,1-dimethyl-2-propynyloxy, 1-methyl-2-butynyloxy, 2-pentymyloxy, 3-pentynyloxy and 4-pentynyloxy.

The addition salts of compounds of formula I with a non-toxic pharmaceutically-acceptable acid possess the same degree of activity as the free bases, from which they are readily prepared by reacting the base with an appropriate acid. Representative of such salts are the mineral acid salts, such as, for instance, the hydrochloride, hydrobromide, sulfate, phosphate and the like and the organic acid salts, such as the succinate, benzoate, acetate, p-toluenesulfonate, benzene sulfonate, maleate, tartrate, methane sulfonate, cyclohexyl sulfonate and the like.

When, in formula I, A represents a —CH$_2$— group, the nomenclature and the numbering of the basic ring systems resulting from each of the different meanings of the moieties (a), (b), (c), (d), and (e) are, respectively, the following:

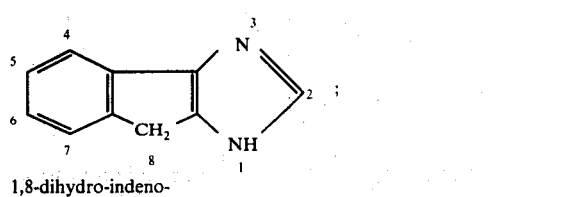

1,8-dihydro-indeno-[1,2-d]imidazole

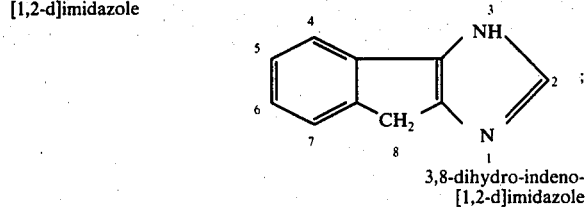

3,8-dihydro-indeno-[1,2-d]imidazole

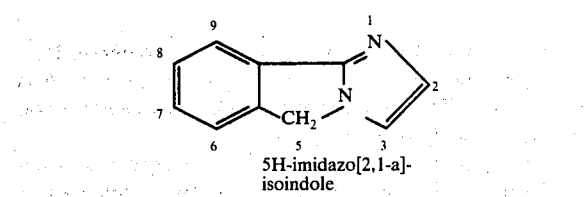

5H-imidazo[2,1-a]-isoindole

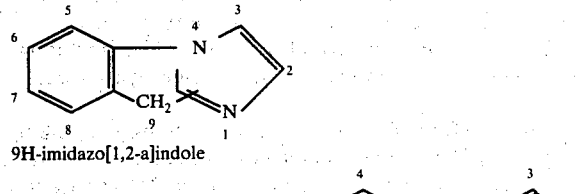

9H-imidazo[1,2-a]indole

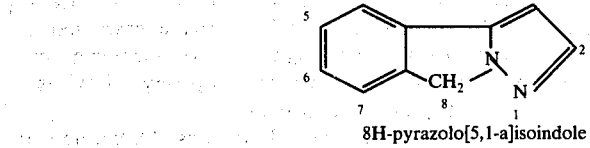

8H-pyrazolo[5,1-a]isoindole

When, in formula I, A represents a —CH═CH— group, the nomenclature and the numbering of the basic ring systems resulting from each of the different meanings of the moieties (a), (b), (c), (d) and (e) are, respectively, the following

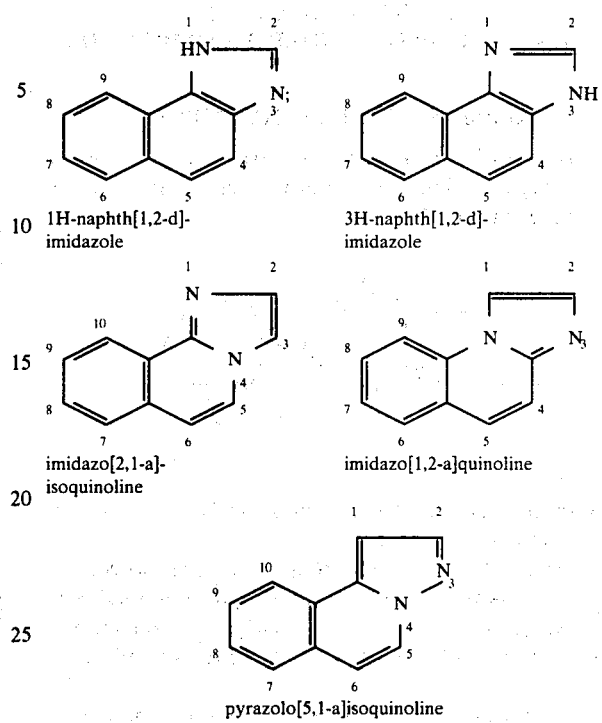

1H-naphth[1,2-d]-imidazole 3H-naphth[1,2-d]-imidazole imidazo[2,1-a]-isoquinoline imidazo[1,2-a]quinoline pyrazolo[5,1-a]isoquinoline When the symbol A in formula I represents —CH$_2$—CH$_2$—, the ring system nomenclature and numbering is obviously the same as in the previous case, the only difference being the appropriate prefix "4,5-dihydro" or "5,6-dihydro" before the name of the ring.

The moieties (a) and (b) when R$_2$ is hydrogen practically identifies the two tautomeric forms of the same compounds of formula I; when R$_2$ is lower alkyl, the two moieties above actually identify two different compounds.

A preferred group of compounds comprise those derivatives of formula I wherein the sequence has one of the following structures

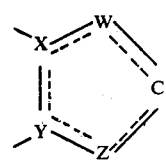

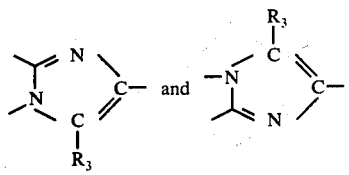

wherein R$_3$ is hydrogen or lower alkyl, A is —CH$_2$—CH$_2$— or —CH═CH—, and at least one of R and R$_1$ (defined as above) is different from hydrogen.

A most preferred group of compounds comprises those compounds wherein the sequence has the following structure

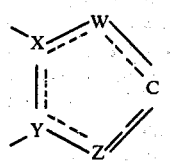

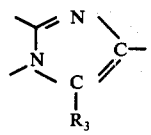

wherein $R_3$ is hydrogen, A is —$CH_2$—$CH_2$— or —CH=CH—; R is located in position 3 or 4 of the phenyl radical and is lower alkoxy, lower alkenyloxy, lower alkynyloxy, cyclopropyloxy, cyclobutyloxy, cyclopentyloxy, cyclohexyloxy, hydroxy, benzyloxy, fluoro, chloro or bromo; and $R_1$ is hydrogen.

DESCRIPTION OF SOME PREFERRED EMBODIMENTS

The process for making the compounds of the invention may follow different schemes depending on the particular meanings which the sequence

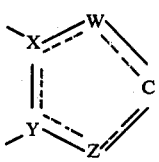

and the symbol A assume.

PREPARATION OF COMPOUNDS HAVING STRUCTURAL MOIETIES (a) and (b)

For preparing 1,8-dihydro-indeno[1,2-d]imidazoles, 3,8-dihydro-indeno[1,2-d]imidazoles, 4,5-dihydro-1H-naphth-[1,2-d]imidazoles, and 4,5-dihydro-3H-naphth[1,2-d]-imidazoles, i.e., compounds for formula I wherein the sequence

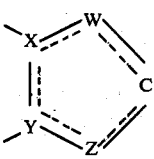

represents a structure identified with (a) or (b) and A is —$CH_2$— or —$CH_2$—$CH_2$—, a cyclic β-haloketone of the formula

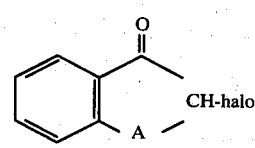

wherein A is —$CH_2$— or —$CH_2$—$CH_2$— and "halo" is bromo or chloro, is reacted with an amidine of the formula

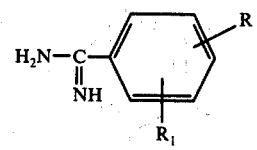

wherein R and $R_1$ have the same meaning as given before.

The reaction is carried out by heating the two reactants together, without any solvent, at 60°–120° C. for 1 to 5 hours, according to the following scheme

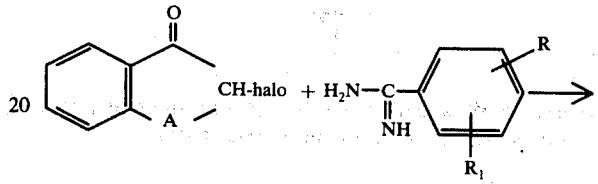

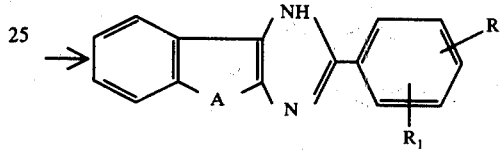

+ H halo
(halo = Cl,Br)

During or before the course of the reaction, a strong base may be added to block the hydrohalide. An excess of the same amidine may also act as the hydrohalide acceptor.

The starting amidine may also be employed in the form of a hydrohalide. In such case, addition of at least one equimolar proportion of a strong base is required to set free the amidine base.

When A represents the group —$CH_2$—, the reaction is preferably carried out in two steps, since by operating under the conditions described immediately above, the reaction course does not go to completion. The second step involves boiling in concentrated acetic acid for 5 to about 60 minutes.

Alkylation of the obtained fused imidazole products on one of the ring nitrogen atoms by means of a lower alkyl sulfate, a lower alkyl halide or tosylate in the presence of a strong base leads to one of the structures (a) and (b) wherein $R_2$ is lower alkyl or to mixtures thereof which may be readily separated into their individual components.

The compounds wherein A represents a —CH=CH— group are obtained by dehydrogenation of the corresponding compound wherein A is —$CH_2$—$CH_2$—.

PREPARATION OF COMPOUNDS HAVING STRUCTURAL MOIETY (C)

For preparing 5H-imidazo[2,1-a]isoindole derivatives, i.e. compounds of formula I wherein the sequence

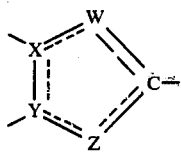

represents the structure identified with (c) and A represents the group —CH$_2$—, a phenacyl halide of the formula

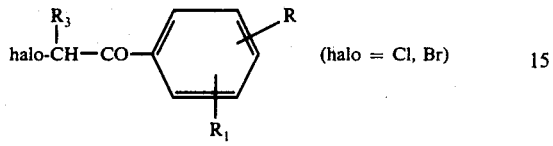

wherein R, R$_1$ and R$_3$ have the same meaning as given before, is reacted with 3-amino-1H-isoindole

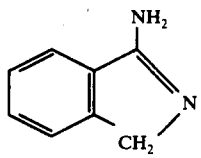

The reaction runs through the following scheme

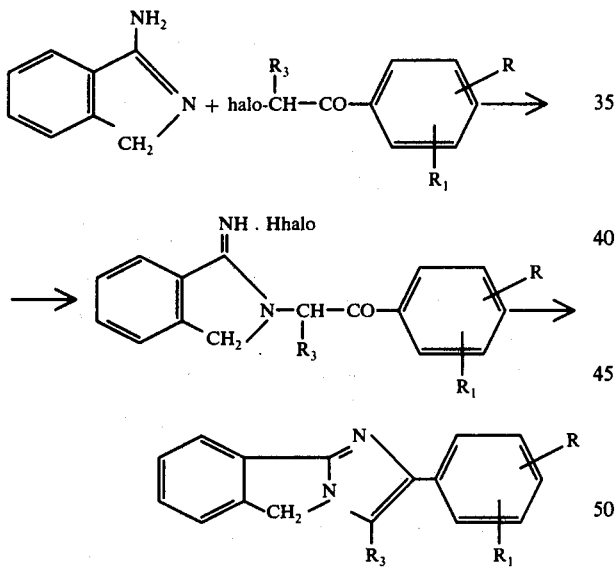

The reaction is carried out in two steps: in the first step, equimolar proportions of the two reagents are brought together at room temperature in the presence of an organic solvent such as dioxane, a liquid chlorinated lower hydrocarbon or benzene. In the second step, which involves cyclization of the intermediate product, the intermediate product is refluxed in a solvent for 3 to 30 hours in the presence of aqueous hydrogen halide such as, for instance, aqueous 10% HCl. An alternative procedure for performing the second step involves transformation of the hydrohalide into a free base by addition thereto of sodium bicarbonate. The free base is then heated at 70°–100° C. for 1 to 4 hours under an inert gas atmosphere with a mixture of ammonium acetate and formamide.

The compounds wherein R is —CH=CH—, i.e. imidazo[2,1-a]isoquinolines, are prepared essentially according to the scheme outlined above by following the procedure described by F. Krohnke et al. in Chem. Ber. 95, 1128 (1962), for the preparation of 2-phenyl-imidazo[2,1-a]isoquinoline.

This method involves reaction of 1-amino-isoquinoline with a phenacyl halide of the formula

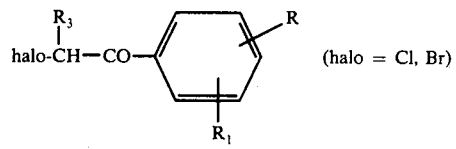

wherein R, R$_1$ and R$_3$ have the same meaning as given before. Hydrogenation of the so-obtained products at 80°–100° C. and 8–15 atmospheres pressure in the presence of a catalyst such as Pd on charcoal leads to the corresponding 5,6-dihydro-imidazo[1,2-a]isoquinoline, i.e. the corresponding compound wherein A is —CH$_2$—CH$_2$—.

PREPARATION OF COMPOUNDS HAVING STRUCTURAL MOIETY (D)

The imidazolo[1,2-a]quinoline derivatives, i.e. the compounds wherein the sequence

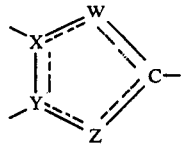

represents the structure identified with (d) and the symbol A is —CH=CH— are prepared according to the method described by F. Krohnke et al. in Chem. Ber. 95, 1128 (1962). This method involves heating an N-phenacylquinolinium halide of the formula

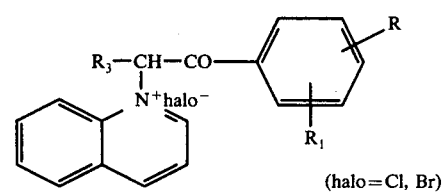

wherein R, R$_1$ and R$_3$ have the same meaning as given before with hydroxylamine in a bomb for 10–30 hours at 100°–150° C.

Catalytic hydrogenation of the so-obtained compounds according to the same conditions described for the corresponding isoquinoline analogs leads to derivatives wherein A is the —CH$_2$—CH$_2$— group, i.e., 4,5-dihydro-imidazo[1,2-a]quinolines.

The compounds wherein A is —CH—$_2$, i.e. 9H-imidazo[1,2-a]indoles, may be prepared by reaction of 2-aminoindole with a phenacyl halide having the same substitutions R, R$_1$ and R$_3$ as above.

PREPARATION OF COMPOUNDS HAVING STRUCTURAL MOIETY (E)

The preparation of a 5,6-dihydro-pyrazolo[5,1-a]isoquinoline, i.e. compounds of formula I wherein the sequence

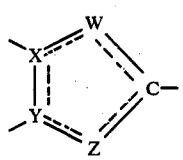

represents the structure identified with (e) and the symbol A is a —$CH_2$—$CH_2$— group, involves reaction of 2-amino-3,4-dihydro-1(2H)-isoquinolinone with a benzoyl acetate according to the following scheme

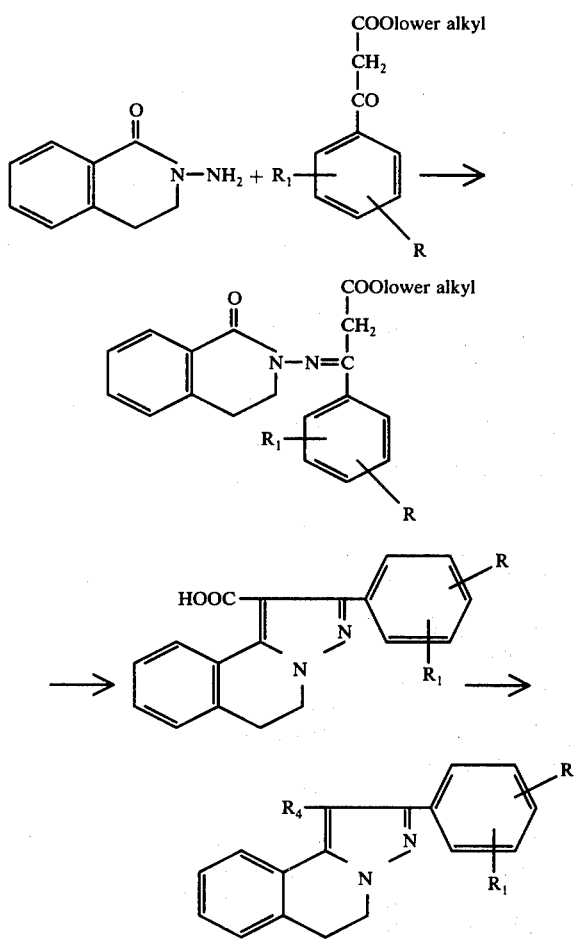

wherein R, $R_1$ and lower alkyl are defined as above.

The first reaction step is carried out by refluxing in an organic solvent such as benzene or toluene equimolar amounts of the two reactants outlined above, in the presence of an acidic catalyst such as p-toluenesulfonic acid or hydrochloric acid. The acid catalyst may be introduced in the reaction mixture as a salt of the same 2-amino-3,4-dihydro-1(2H)-isoquinolinone.

The so-obtained Schiff's base is then cyclized to 5,6-dihydro-pyrazolo[5,1-a]isoquinoline-1-carboxylic acid by refluxing it in a lower alkanol in the presence of a strong base such as, for instance, an alkali metal lower alkoxide.

The carboxylic acid derivative is then converted into the other compounds of formula I wherein $R_4$ has meanings different from carboxy; For instance, refluxing in ethanol with concentrated sulfuric acid leads to decarboxylated compounds ($R_4$=H).

The compounds wherein $R_4$ represents carbamyl or mono- or di-(lower alkyl)carbamyl or carbo(lower alkoxy) are obtained by transforming the carboxylic acid compound into the corresponding chloride which in turn is reacted with ammonia, a mono- or di- lower alkyl amine or a lower alkanol. Esterification of the carboxy group with a lower alkyl iodide in dimethylformamide in the presence of an alkali metal bicarbonate is an alternative procedure to obtain a carboxy ester. [$R_4$=carbo(lower alkoxy)].

Reduction of the ester with an alkali metal aluminum hydride leads to hydroxymethyl derivatives ($R_4$=hydroxymethyl). Transformation of the hydroxymethyl function into halomethyl and then hydrogenolysis by means of a mixture of an alkali metal hydride and an alkali metal aluminum hydride leads to compounds wherein $R_4$ is methyl.

Dehydrogenation of the 5,6-dihydropyrazolo[5,1-a]isoquinoline affords the corresponding compounds wherein A is —CH=CH—. N-bromacetamide, sulfur, bromine, lead tetraacetate, mercuric acetate, chloranil, dichlorodicyanoquinone and manganese dioxide are suitably employed as the dehydrogenating agents. Generally the reaction is carried out in the presence of a solvent, which is preferably selected from inert organic liquids, as, for instance, benzene, dioxane, tetrahydrofuran, carbon tetrachloride and the like. The dehydrogenating agent may be added in the same proportion as the starting compound or in a considerably large molar excess.

By following the reaction scheme outlined above but employing N-aminophthalimidine as the starting material instead of 2-amino-3,4-dihydro-1(2H)-isoquinolinone, the corresponding compounds wherein A is —$CH_2$—, i.e., 8H-pyrazolo[5,1-a]isoindoles are obtained. More advantageously, the latter compounds are prepared by cyclization of a pyrazole of the formula

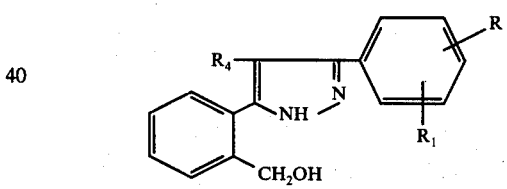

wherein R, $R_1$ and $R_4$ have the same meaning as given before.

For promoting the cyclization, the hydroxymethyl function is transformed into a group more reactive towards the ring nitrogen atom. For example, it may be transformed into a halomethyl, a mesyloxymethyl, or a tosyloxymethyl group. The so-obtained compound is then refluxed in an organic solvent in the presence of an alkali metal lower alkoxide or amide to perform the cyclization step. The solvent of the reaction is preferably selected from a lower alkanol, benzene or toluene. The time of the reaction may range from 20 minutes to 3 to 4 hours and the temperature may vary between 40° C. and the boiling temperature of the reaction mixture.

In all cases described above when a compound of formula I is obtained, where the radical R is benzyloxy, it may be transformed thrugh hydrogenolysis into the corresponding hydroxy derivative. Alternatively, the latter may be prepared from the corresponding lower alkoxy derivative through dealkylation by refluxing with HBr in acetic acid.

The compounds of formula I wherein the radical R is lower alkyloxy, lower alkenyloxy, lower alkynyloxy, cyclopropyloxy, cyclobutyloxy, cyclopentyloxy or cyclohexyloxy, may also be prepared by reaction of the corresponding hydroxy derivative with suitable agents such as the lower alkyl, lower alkenyl, lower alkynyl, cyclopropyl, cyclobutyl, cyclopentyl, cyclohexyl halogenides, tosylates or mesylates.

The compounds of this invention show very interesting post-coital post-implantation anti-fertility activity when administered subcutaneously or orally to laboratory animals, e.g. rats, hamsters, dogs and monkeys. Moreover, the abortifacient activity of the new compounds is not accompanied by other biological effects which are usually associated with hormonal substances. Thus, an entirely new approach to fertility regulation is provided in which a non-hormonal compound can be administered parenterally or orally on a one or more times per month basis or as needed for a "missed period" or to induce termination of a more advanced pregnancy.

Representative experiments for assessing antifertility activity are carried out with female Syrian golden hamsters weighing 100 to 130 g. The animals are mated and the presence of sperm in the vagina is taken as evidence of mating. The day sperm are detected is considered day one of pregnancy, since in our laboratories and those of other investigators 90 to 100% of animals that mate, as evidenced by vaginal sperm, are pregnant. Pregnancy is later confirmed at time of autopsy by presence of fetuses or implantation sites in the uterus. Even if an animal aborts the fetuses, implantation scars still remain as evidence that the animal had been pregnant.

Test compounds dissolved or suspended in sesame oil are administered subcutaneously in doses of 10 mg/kg. daily for 5 days beginning on day 4 of pregnancy (days 4–8). The animals are autopsied on day 14 of pregnancy and the uteri are examined for evidence of pregnancy (implantation sites, fetal resorptions or live fetuses, hemorrhage, and evidence of abnormalities of the uterus, placenta or fetuses). A compound is considered to be active if there is a reduction of live fetuses in at least 60% of the treated animals and the presence of implantation sites proves the animal to have been pregnant. In representative experiments the compound of the following Examples proved to be active according to the above mentioned criteria: 4, 5, 6, 7, 8, 9, 12, 13, 14, 15, 16, 17, 18, 19, 20, 23, 24, 25, 26, 29, 31, 36, 40, 41 and 46.

The compounds are then studied for dose-activity relationship and toxicity or other biological activities. Compounds that show 100% effectiveness (absence of live fetuses in 100% of animals) with minimal side effects or toxicity are studied in depth.

The following Table shows the typical dose responses to some of the highly effective anti-fertility compounds of this invention.

TABLE I

| Compound | Dose mg/kg/day | No. of hamsters | No. % animals aborting |
|---|---|---|---|
| 2-(4-chlorophenyl)imidazo-[2,1-a]isoquinoline | 0.25(s.d.) | 12 | 100 |
|  | 0.125(s.c.) | 6 | 100 |
|  | 0.062(s.c.) | 15 | 93.3 |
|  | 0.031(s.c.) | 10 | 30 |
|  | 0.016(s.c.) | 10 | 0 |
|  | 20 (os) | 4 | 100 |
|  | 5 (os) | 10 | 80 |
|  | 2.5(os) | 6 | 0 |
| 2-(4-bromophenyl)imidazo-[2,1-a]isoquinoline | 0.25(s.c.) | 11 | 100 |
|  | 0.125(s.c.) | 6 | 100 |
|  | 0.062(s.c.) | 15 | 73.3 |
|  | 0.031(s.c.) | 10 | 10 |
|  | 20 (os) | 4 | 100 |
|  | 5 (os) | 10 | 60 |
|  | 2.5(os) | 6 | 0 |
| 2-(4-fluorophenyl)imidazo-[2,1-a]isoquinoline | 1 (s.c.) | 6 | 100 |
|  | 0.1 (s.c.) | 11 | 63.6 |
|  | 0.05(s.c.) | 5 | 0 |
| vehicle (blank) | — | 21 | 0(contained 95% live fetuses) |

The same criteria and conditions are also employed with rats, with the exception that the animals (female Sprague-Dawely rats weighing 200–230 g.) are treated on days 6 through 10 of pregnancy with a screening dose of 20 mg/kg s.c. daily and are autopsied on day 16.

The compounds may be administered by various routes, for example, orally, subcutaneously, intravenously or intramuscularly. For oral administration the compounds are compounded in such forms as tablets, dispersible powders, capsules, syrups, and solutions. Tablets may contain the active ingredient admixed with conventional pharmaceutically acceptable excipients, e.g., inert diluents, such as calcium carbonate, sodium carbonate, lactose and talc, granulating and disintegrating agents, such as starch, alginic acid and sodium carboxymethylcellulose, binding agents, e.g., starch, gelatin, gum-arabic and polyvinylpyrrolidone and lubricating agents, e.g., magnesium stearate, stearic acid and talc. Syrups and solutions are formulated in ways known in the art. Together with the active compound, they may contain suspending agents, such as for instance, methylcellulose, hydroxyethylcellulose, tragacanth and sodium alginate, wetting agents, e.g., lecithin, polyoxyethylene stearates and polyoxyethylene sorbitan monooleate, and the common preservative, sweetening and buffering agents. A capsule or a tablet may contain the active ingredient alone or admixed with an inert solid diluent, such as, for instance, calcium carbonate, calcium phosphate or kaolin.

For intravenous or intramuscular administration, the active ingredient is embodied in injectable dosage forms, which may contain appropriate dispersing or wetting agents and suspending or buffering agents identical or similar to those mentioned above. Sesame oil, benzyl alcohol, benzyl benzoate, peanut oil and their mixtures may be suitably employed as vehicles when the compounds are scarcely soluble in aqueous media.

The dosage of active ingredients employed for inhibiting reproduction may vary, depending on the compound used, on the type of animal treated and on the duration of the treatment. Generally, good results are obtained by administering to the animal for one to five days a compound of formula I at a daily dosage of from about 0.05 mg/kg to about 25 mg/kg.

The following additional description and examples further describe the invention and the manner and process of making and using it to enable the art skilled to make and use the same and set forth the best mode contemplated by the inventors of carrying out the invention.

EXAMPLE 1

2-Phenyl-4,5-dihydro-naphth[1,2-d]imidazole hydrochloride

Seven grams of benzamidine and 6.75 grams of 2-bromo-1-tetralone are heated at 70° C. for three hours. The reaction mixture after cooling is dissolved in dichloromethane and the organic layer is washed with water and dried over $Na_2SO_4$. Evaporation to dryness of the solution gives 8 g. of 2-phenyl-4,5-dihydro-naphth[1,2-d]imidazole. M.p. 220° C. (from isopropyl ether).

By addition of ethyl ether saturated with HCl to an ethanol solution of the reaction compound, the corresponding hydrochloride is obtained in a 95% yield. The hydrochloride does not melt up to 300° C.

EXAMPLE 2 a. 1-methyl-2-phenyl-4,5-dihydro-naphth[1,2-d]imidazole and
b. 3-methyl-2-phenyl-4,5-dihydro-naphth[1,2-d]imidazole To 2-phenyl-4,5-dihydro-naphtho[1,2-d]imidazole (2.46 g.) dissolved in 10 ml. of dimethylformamide, 0.5 g. of 55% NaH (mineral oil dispersion) and 1.41 g. of methyl iodide are added. After stirring for two hours at room temperature, and for one hour at 60° C., the mixture is poured into ice water. The resulting solid precipitate is dissolved in benzene and chromatographed through a silica gel column and eluted with benzene containing 10% of ethyl ether for separating the two methylated isomers. The first eluted isomer (1.66 g.) melts at 150° C. (from ethanol) while the second (0.79 g.) melts at 141°-3° C. By operating according to the procedure described in Example 1, utilizing as the starting material 2-bromo-1-indanone, 2-phenyl-1,8-dihydro-indeno[1,2-d]imidazole (m.p. 231-2) is obtained which is in turn methylated according to the procedure described above to give 1-methyl-2-phenyl-8H-indeno[1,2-d]-imidazole, 3-methyl-2-phenyl-8-indeno[1,2-d]imidazole.

EXAMPLE 3

2-Phenyl-5H-imidazo[2,1-a]isoindole

To a solution of 6.8 g. of 3-amino-1H-isoindole in 100 ml. of dichloromethane, 10.25 g. of phenacyl bromide in 50 ml. of dichloromethane is added. After stirring for 30 minutes, the solution is concentrated to a small volume and cooled. The resulting solid precipitated (3-amino-2-phenacyl-1H-isoindole hydrobromide, m.p. 221°-3° C.) is collected on a filter and cyclized by refluxing for 24 hours in a mixture of 150 ml. of ethanol and 100 ml. of 8% HCl. The reaction mixture is cooled to about 0° C. and the solid which precipitates is recovered by filtration. Crystallization from ethanol containing 8% HCl gives 2.27 g. of product, the hydrochloride of 2-phenyl-5H-imidazo[2,1-a]isoindole with ½ molecule of water of crystallization. The free base, obtained by treatment of the latter with aqueous sodium carbonate and crystallization from isopropyl ether, melts at 152°-3° C.

An alternative cyclization procedure involves heating 4 g. of 3-amino-2-phenacyl-1H-isoindole (obtained by alkalinization of the corresponding hydrobromide with aqueous sodium bicarbonate) with 120 ml. of formamide and 2.46 g. of ammonium acetate for 3 hours at 85° C. under an argon atmosphere. Yiel 1.85 g. of the title compound.

EXAMPLE 4

2-(4-methoxyphenyl)-imidazo[2,1-a]isoquinoline

To a solution of 1-aminoisoquinoline (10.1 g.) in 10 ml. of $CHCl_3$, a solution of ω-bromo-p-methoxyacetophenone (16.35 g.) in 30 ml. of $CHCl_3$ is added. After 15 minutes at room temperature, the chloroform is evaporated off and the residue is heated at 100° C. for an additional fifteen minutes under vacuum. After cooling, the solid product which forms is dissolved in 400 ml. of hot methanol and the obtained solution is poured into 500 ml. of ice-cooled ethyl ether. The solid which precipitates (22.57 g.) is the hydrobromide of the title product, m.p. 254°-55° C. (with decomposition).

Six grams of the hydrobromide are added to 80 ml. of ammonium hydroxide in the presence of 250 ml. of dichloromethane. The organic phase is washed with water, dried over sodium sulfate and evaporated to dryness. The residue is crystallized from ethanol, yielding 4.41 g. of the title product which melts at 177°-9° C.

EXAMPLES 5-19

By following essentially the same procedure as in Example 4 and employing phenylalkanones having the indicated substituents on the phenyl ring, the following compounds are obtained:

(5) 2-(2-methoxyphenyl)imidazo[2,1-a]isoquinoline M.p. 157°-8° C.
(6) 2-(3-methoxyphenyl)imidazo[2,1-a]isoquinoline M.P. 100°-1° C.
(7) 2-(p-tolyl)imidazo[2,1-a]isoquinoline M.p. 161°-3° C.
(8) 2-(p -chlorophenyl)imidazo[2,1-a]isoquinoline M.p. 193°-4° C.
(9) 2-(p-bromophenyl)imidazo[2,1-a]isoquinoline M.p. 205°-6° C.
(10) 2-(2,5-dimethoxyphenyl)imidazo[2,1-a]isoquinoline M.p. 154°-5° C.
(11) 3-methyl-2-phenylimidazo[2,1-a]-isoquinoline M.p. 177°-8° C.
(12) 2-(4-fluorophenyl)imidazo[2,1-a]isoquinoline M.p. 162°-4° C.
(13) 2-(2-chlorophenyl)imidazo[2,1-a]isoquinoline M.p. 122°-3° C.
(14) 2-(3-chlorophenyl)imidazo[2,1-a]isoquinoline M.p. 150°-1° C.
(15) 2(3,4-dichlorophenyl)imidazo[2,1-a]isoquinoline M.p 160°-1° C.
(16) 2-(4-nitrophenyl)imidazo[2,1-a]isoquinoline M.p. 245°-6° C.
(17) 2-(3-ethoxyphenyl)imidazo[2,1-a]isoquinoline M.p. 102°-3° C.
(18) 2-(3-propoxyphenyl)imidazo[2,1-a]isoquinoline M.p. 65°-7° C.
(19) 2-(3-allyloxyphenyl)imidazo[2,1-a]isoquinoline M.p. 83°-5° C.

Other compounds which may be prepared according to the procedure previously described above are the following:

2-(3-fluorophenyl)imidazo[2,1-a]isoquinoline,
2-(3-bromophenyl)imidazo[2,1-a]isoquinoline,
2-(4-iodophenyl)imidazo[2,1-a]isoquinoline,
2-(3-cyclopentyloxyphenyl)imidazo[2,1-a]isoquinoline, 2-(3-propargyloxyphenyl)imidazo[2,1-a]isoquinoline,
2-(3,4-dibromophenyl)imidazo[2,1-a]isoquinoline,
2-(3-pentyloxyphenyl)imidazo[2,1-a]isoquinoline,
2-(3-trifluoromethylphenyl)imidazo[2,1-a]isoquinoline,
2-(4-trifluoromethylphenyl)imidazo[2,1-a]isoquinoline,
3-methyl-2-(4-chlorophenyl)imidazo[2,1-a]isoquinoline,
3-methyl-2-(4-bromophenyl)imidazo[2,1-a]isoquinoline,
2-(3-butoxyphenyl)imidazo[2,1-a]isoquinoline,
2-(3-cyanophenyl)imidazo[2,1-a]isoquinoline,
2-(4-cyanophenyl)imidazo[2,1-a]isoquinoline; M.p. 188–189° C.
2-(3-sulfamoylphenyl)imidazo[2,1-a]isoquinoline,
2-(4-sulfamoylphenyl)imidazo[2,1-a]isoquinoline and
2-(3,4-methylenedioxyphenyl)imidazo[2,1-a]isoquinoline; M.p. 168, 171° C.

EXAMPLE 20

2-(3-Hydroxyphenyl)imidazo[2,1-a]isoquinoline 2-(3-Methoxyphenyl)imidazo[2,1-a]isoquinoline (11 g.) is refluxed for four hours in a mixture of 100 ml. of acetic acid and 100 ml. of 48 percent hydrobromic acid. The reaction mixture is evaporated to dryness and the residue is taken up with 200 ml. of water and 20 ml. of 30 percent sodium hydroxide. After filtration, the filtered solution is extracted with dichloromethane and the aqueous phase is neutralized with dilute hydrochloric acid. The resulting solid precipitate is collected by filtration and crystallized from dichloromethane. Yield 9 g. of the title product which melts at 201°–2° C.

EXAMPLE 21

2-(3-Ethoxyphenyl)imidazo[2,1-a]isoquinoline 2-(3-Hydroxyphenyl)imidazo[2,1-a]isoquinoline (2.07 g.) is added to 0.63 g. of 85 percent potassium hydroxide in 25 ml. of ethanol. To this mixture, 1.56 ml. of diethyl sulfate in 5 ml. of ethanol is added at 0° to 5° C. The mixture is maintained for 16 hours at room temperature, then is refluxed for 30 minutes. After cooling, the solution is evaporated to dryness and the residue is washed thoroughly with water. Crystallization of the solid from ethanol yields 1 g. of the title product, melting at 102°–3° C.

EXAMPLE 22

2(3-Allyloxyphenyl)imidazo[2,1-a]isoquinoline

By operating according to the procedure of the previous Example, employing allylbromide instead of diethyl sulfate, the title compound is obtained, melting at 83°–5° C.

EXAMPLE 23

2-(4-Methoxyphenyl)-5,6-dihydro-imidazo[2,1-a]isoquinoline

To a one liter autoclave are charged 7.1 g. of 2-(4-methoxyphenyl)imidazo[2,1-a]isoquinoline, 210 ml. of ethanol, 150 ml. of acetic acid and 0.55 g. of 10% palladium on charcoal. After flushing and filling the autoclave with hydrogen, the mixture is hydrogenated at 90° C. and 10 atmospheres for 3 hours. After absorption of 1.5 atmospheres of hydrogen gas, the autoclave is cooled and vented and 200 ml. of $CHCl_3$ is added to the reaction mixture. The catalyst is filtered off, and the solution is evaporated to dryness, giving a solid residue which is suspended in 10% ammonium hydroxide, then extracted with dichloromethane. After drying over $Na_2SO_4$, the organic solvent is evaporated off and the residue is crystallized from ethanol giving 4.55 g. of the title product, which melts at 179°–81° C.

EXAMPLES 24–28

By hydrogenating the corresponding imidazo[2,1-a]isoquinolines according to the procedure of Example 23, the following 5,6-dihydro compounds are obtained:

(24) 2-(p-tolyl)-5,6-dihydro-imidazo[2,1-a]isoquinoline M.p. 143°–5° C.

(25) 2-(2-methoxyphenyl)-5,6-dihydro-imidazo[2,1-a]isoquinoline M.p. 158°–61° C.

(26) 2-(3-methoxyphenyl)-5,6-dihydro-imidazo[2,1-a]isoquinoline M.p. 92°–4° C.

(27) 2-(2,5-dimethoxyphenyl)-5,6-dihydro-imidazo[2,1-a]isoquinoline M.p. 126°–8° C.

(28) 3-methyl-2-phenyl-5,6-dihydro-imidazo[2,1-a]isoquinoline M.p. 163°–4° C.

Other compounds which may be prepared according to the procedure just described are the following:

2-(3-hydroxyphenyl)-5,6-dihydro-imidazo[2,1-a]isoquinoline, 2-(3-ethoxyphenyl)-5,6-dihydro-imidazo[2,1-a]isoquinoline, 2-(3-propoxyphenyl)-5,6-dihydro-imidazo[2,1-a]isoquinoline, 2-(3-butoxyphenyl)-5,6-dihydro-imidazo[2,1-a]isoquinoline and 2-(3,4-methylenedioxyphenyl)-5,6-dihydro-imidazo[2,1-a]-isoquinoline.

EXAMPLE 29

2-(3-Methoxyphenyl)-imidazo[1,2-a]quinoline

A solution of 9.6 g. of quinoline and 17.2 of ω-bromo-m-methoxyacetophenone in 150 ml. of anhydrous benzene is refluxed for 16 hours. After cooling, the resulting solid precipitate, [1-(3-methoxyphenacyl)-quinolinium bromide], is recovered on a filter and washed with benzene. Yield 26.8 g., m.p. 236°–8° C.

In a steel bomb having an internal glass coating, 9.34 g. of 1-(3-methoxyphenacyl)quinolinium bromide is heated at 130° C. for 24 hours together with 2.17 g. of hydroxylamine hydrochloride dissolved in 39 ml. of water. After cooling, the resulting solid precipitate is boiled with 60 ml. of water and recovered by filtration. The solid product is suspended in 50 ml. of water and concentrated ammonium hydroxide is added to the suspension. The mixture is extracted with dichloromethane and the organic extract is evaporated to dryness. By crystallization from methanol, 4.5 g. of the title product is obtained which melts at 129°–31° C.

Pursuant to the procedure of Example 29, the following compounds are prepared:
2-(4-chlorophenyl)imidazo[1,2-a]quinoline,
2-(4-bromophenyl)imidazo[1,2-a]quinoline,
2-(p-tolyl)imidazo[1,2-a]quinoline,
2-(4-trifluoromethylphenyl)imidazo[1,2-a]quinoline,
2-(3,4-dichlorophenyl)imidazo[1,2-a]quinoline,
2-(3-ethoxyphenyl)imidazo[1,2-a]quinoline,
2,(3-allyloxyphenyl)imidazo[1,2-a]quinoline and
2-(3-propargyloxyphenyl)imidazo[1,2-a]quinoline.

EXAMPLE 30

2-(3-Methoxyphenyl)-4,5-dihydro-imidazo[1,2-a]quinoline 2-(3-Methoxyphenyl)imidazo[1,2-a]quinoline (2.74 g) together with 0.5 g. of 10% palladium on charcoal, 35 ml. of ethanol and 25 ml. of acetic acid is hydrogenated at 90° C. and 10 atmospheres for five hours. After filtration of the catalyst, the solution is evaporated to dryness and the residue is washed with water and aqueous solution carbonate. The resulting solid is extracted with ethyl ether and the organic solution, after drying, is evaporated to yield a product which, after crystallization from a hexane dichloromethane mixture, melts at 107°–9° C.

EXAMPLE 31

2-Phenyl-4,5-dihydro-imidazo[1,2-a]quinoline

The title product is obtained from the corresponding unsaturated compound by the procedure of Example 30, b.p. 160°/0.03 mm Hg. The corresponding hydrochloride is obtained by bubbling dry HCl into an ethanol solution of the free base; m.p. 315° C. (with decomposition).

EXAMPLE 32

2-(3-Methoxyphenyl)-5,6-dihydro-pyrazolo[5,1-a]isoquinoline-1-carboxylic acid

2-Amino-3,4-dihydro-isoquinoline-1(2H)-one, (7.3 g), ethyl (m-methoxybenzoyl)acetate (10 g.) and a catalytic amount of 2-amino-3,4-dihydro-isoquinoline-1(2H)-one p-toluensulfonate (1.58 g.) are refluxed for 3 hours in 100 ml. of benzene using a Dean and Stark apparatus. After cooling, 200 ml. of ethyl ether is added to the mixture which is then filtered. The filtrate is evaporated to dryness giving 15.82 g. of the Schiff's base product. (b.p. 200°–210° C./0.01 mm Hg)

A solution of 14.65 g. of the Schiff's base in 150 ml. of tert-butanol is added to 350 ml. of tert-butanol wherein 3.12 g. of potassium have been previously dissolved.

The mixture is refluxed for 10 hours and then the solvent is evaporated off. The residue is dissolved in water and the aqueous solution is acidified with concentrated HCl to yield 10.64 g. of the title product which melts at 190° C. with decompositon after crystallization from methanol.

EXAMPLES 33–34

Pursuant to the procedure of Example 32, the following compounds are prepared:

2-Phenyl-5,6-dihydro-pyrazole[5,1-a]isoquinoline-1-carboxylic acid M.p. 208°–10° C. (with decomposition)

(34) 2-(m-Benzoyloxyphenyl)-5,6-dihydro-pyrazole[5,1-a]-isoquinoline-1-carboxylic acid M.p. 205°–9° C. (with decomposition)

EXAMPLE 35

2-(m-Methoxyphenyl)-5,6-dihydro-pyrazole[5,1-a]isoquinoline 2-(m-Methoxyphenyl)-5,6-dihydro-pyrazole[5,1-a]isoquinoline-1-carboxylic acid (7.18 g.) is refluxed for 21 hours in 315 ml. of 95% ethanol containing 3.59 ml. of sulfuric acid. The solvent is evaporated off and the residue is washed subsequently with aqueous sodium carbonate and water. After extraction with dichloromethane, the organic solution is washed with water, then evaporated to dryness. The residue is crystallized from isopropyl ether, giving 6 g. of the title product which melts at 92°–3° C.

EXAMPLES 36–37

By following the same procedure as in Example 35, the following compounds are prepared:
(36) 2-Phenyl-5,6-dihydro-pyrazolo[5,1-a]isoquinoline M.p. 88°–9° C.

(37) 2-(m-Benzyloxyphenyl)-5,6-dihydro-pyrazole[5,1-a]isoquinoline M.p. 106°–7° C.

EXAMPLE 38

2-(m-Hydroxyphenyl)-5,6-dihydro-pyrazolo[5,1-a]isoquinoline

Eighty grams of 2-(m-benzyloxyphenyl)-5,6-dihydropyrazolo[5,1-a]isoquinoline is hydrogenated at room temperature and atmospheric pressure in 3500 ml. of methanol in the presence of 15 g. of 10% palladium on charcoal. When the theoretical amount of hydrogen is consumed, the mixture is filtered and the filtrate is evaporated to dryness, giving 53.98 g. of solid which, after crystallization from ethanol, gives the title compound which melts at 177°–9° C.

EXAMPLE 39

2-(m-Ethoxyphenyl)-5,6-dihydro-pyrazolo[5,1-a]isoquinoline 2-(m-Hydroxyphenyl)-5,6-dihydro-pyrazolo[5,1-a]-isoquinoline (5.24 g) is added with stirring to 100 ml. of anhydrous ethanol wherein 0.5 g. of sodium has previously been dissolved. Then 4.67 g. of ethyl iodide is added to the reaction mixture and stirring is continued for one hour at room temperature and for 20 hours at 60° C. After evaporation of the ethanol, diethyl ether is added to the residue and the organic layer is washed with aqueous 2% NaOH, then with water. The ether solution is dried over sodium sulfate and evaporated to give 5.1 g. of the title product which, after crystallization from isopropyl alcohol, melts at 103°–4° C.

EXAMPLE 40

2-(m-Methoxyphenyl)pyrazolo[5,1-a]isoquinoline

To a solution of 2.5 g. of 2-(m-methoxyphenyl)-5,6-dihydro-pyrazolo[5,1-a]isoquinoline in 100 ml. of benzene is gradually added with stirring 30 g. of $MnO_2$ prepared as described by E. Pratt et al., J. Org. Chem. 26, 2973 (1961) and activated according to the procedure of J. M. Goldman, J. Org. Chem. 34, 1979 (1969). The obtained mixture is refluxed with stirring for five days, then filtered. The filtrate after evaporation and crystallization of the solid residue from isopropyl ether gives 1 g. of the title product, m.p. 109°–11° C.

EXAMPLE 41

2-Phenylpyrazolo[5,1-a]isoquinoline

The compound is prepared according to the procedure of Example 40 starting with the corresponding 5,6-dihydro derivative. M.p. 120°–1° C.

Pursuant to the preceding procedures, the following pyrazolo[5,1-a]isoquinolines are obtained:
2-(4-chlorophenyl)pyrazolo[5,1-a]isoquinoline;
2-(4-bromophenyl)pyrazolo[5,1-a]isoquinoline;
2-(4-fluorophenyl)pyrazolo[5,1-a]isoquinoline;
2-(4-iodophenyl)pyrazolo[5,1-a]isoquinoline;
2-(4-trifluoromethylphenyl)pyrazolo[5,1-a]isoquinoline;
2-(3,4-dichlorophenyl)pyrazolo[5,1-a]isoquinoline;
2-(3-propoxyphenyl)pyrazolo[5,1-a]isoquinoline;
2-(3-allyloxyphenyl)pyrazolo[5,1-a]isoquinoline;
2-(3-propargyloxyphenyl)pyrazolo[5,1-a]isoquinoline;
2-(3-pentyloxyphenyl)pyrazolo[5,1-a]isoquinoline;
2-(4-cyanophenyl)pyrazolo[5,1-a]isoquinoline and
2-(4-sulfamoylphenyl)pyrazolo[5,1-a]isoquinoline.

EXAMPLE 42

2-Phenyl-5,6-dihydro-pyrazolo[5,1-a]isoquinoline-1-carboxylic acid ethyl ester

19

2-Phenyl-5,6-dihydro-pyrazolo[5,1-a]isoquinoline-1-carboxylic acid (7.48 g.) is stirred at 90° C. for three hours with 3.77 ml. of SOCl$_2$. The thionyl chloride excess is eliminated in vacuo and the residual acid chloride is dissolved in 80 ml. of ethanol at 40°–50° C. After 15 minutes, the reaction mixture is neutralized by addition of aqueous sodium bicarbonate and the solvent is eliminated by distillation. The residue is extracted with ethyl ether and, after evaporation of the organic solution, is crystallized from isopropyl ether. Yield of title compound 2.47 g.; m.p. 84°–5° C.

EXAMPLE 43

2-Phenyl-5,6-dihydro-pyrazolo[5,1-a]isoquinoline-1-carboxylic acid methyl ester

The compound is prepared according to the procedure of Example 42 but employing methanol instead of ethanol; m.p. 112°–3° C.

EXAMPLE 44

N,N-diethyl-2-phenyl-5,6-dihydro-pyrazolo[5,1-a]isoquinoline-1-carboxamide

To a solution of 4.4 g. of 2-phenyl-5,6-dihydropyrazolo[5,1-a]isoquinoline-1-carbonyl chloride (obtained according to the procedure of Example 42) in 25 ml. of anhydrous benzene is added 4 ml. of N,N-diethylamine. After 15 minutes, the solvent is distilled off and the residue is washed with water and crystallized from isopropyl ether yielding 3.78 g. of the title product, which melts at 109°–10° C.

EXAMPLE 45

2-Phenyl-5,6-dihydro-pyrazolo[5,1-a]isoquinoline-1-methanol

To 0.76 g. of LiAlH$_4$ in 50 ml. of tetrahydrofuran, 6.08 g. of the methyl ester of 2-phenyl-5,6-dihydropyrazolo[5,1-a]isoquinoline-1-carboxylic acid dissolved in 75 ml. of tetrahydrofuran is added. The mixture is stirred for four hours at room temperature, then refluxed for one hour. To the reaction mixture at about 0° C. are subsequently added 0.76 ml. of water, 0.76 ml. of 20% NaOH and again 2.3 ml. of water. After addition of 75 ml. of ethyl ether, the inorganic precipitate is filtered off and the organic solution is evaporated to dryness to give 4 g. of the title product which, crystallized from ethanol, melts at 185°–7° C.

EXAMPLE 46

1-Methyl-2-phenyl-5,6-dihydro-pyrazolo[5,1-a]isoquinoline

Dry hydrogen bromide is bubbled to complete saturation into a solution of 2.95 g. of 2-phenyl-5,6-dihydropyrazolo[5,1-a]isoquinoline-1-methanol in 150 ml. of acetic acid. The mixture is heated at 60° C. for 21 hours and the acetic acid is evaporated off to give 4 g. of 1-bromomethyl-2-phenyl-5,6-dihydro-pyrazolo[5,1-a]isoquinoline hydrobromide, m.p. 196°–214° C.

To 1.72 g. of the latter compound in 50 ml. of tetrahydrofuran are added 0.25 g. of LiH in 20 ml. of tetrahydrofuran under stirring at room temperature. To the obtained mixture are added 0.5 g. of LiAlH$_4$ and stirring is continued for further 10 hours. After cooling to about 0° C. the following additions are subsequently made: 10 ml. of tetrahydrofuran containing 20% water; 1 ml. of 30% NaOH and, finally, 10 ml. of water. The inorganic salts are filtered off and the filtrate is evaporated to give 1.13 g. of a residue which is purified by crystallization from iospropyl ether. Yield 1.08 g. of the title product having m.p. 122°–4° C.

EXAMPLE 47

2-Phenyl-8H-pyrazolo[5,1-a]isoindole

A solution of 15 g. 3-phenyl-5-[2-(hydroxymethyl)-phenyl]pyrazole in 300 ml. of acetic acid saturated with dry hydrogenbromide is maintained at 20° C. for 21 hours. The solid precipitate which forms, i.e. the hydrobromide of 3-phenyl-5-[2-(bromomethyl)phenyl]-pyrazole, is recovered by filtration. Yield 22.5 g.; m.p. 267°–8° C. (with decomposition).

17.5 Grams of the so-obtained hydrobromide in 300 ml. of ethanol is added to 300 ml. of ethanol wherein 2.07 g. of sodium has previously been dissolved. The mixture is refluxed for one hour, then the solvent is eliminated by distillation. The residue is extracted with dichloromethane and washed with water. The resulting organic solution, after drying over Na$_2$SO$_4$, is evaporated and the residue is crystallized from isopropanol. Yield 6.48 g. of the title product, melting at 183°–4° C.

Preparation of the Intermediate
3-Phenyl-5-[2-(hydroxymethyl)-phenyl]-pyrazole

1-Phenyl-3-(o-tolyl)-1,3-propanedione (b.p. 170° C./0.01 mm Hg) is condensed with hydrazine in ethanol to give 3-phenyl-5-(o-tolyl)pyrazole, m.p. 112.5°–113.5° C.

The latter compound is oxidized to 3-phenyl-5-(2-carboxyphenyl)pyrazole (m.p. 201°–4° C.) with potassium permanganate in the presence of an equimolar amount of potassium hydroxide. Aqueous pyridine (50%) is employed as the solvent. Then the carboxylic acid function is transformed into the corresponding methyl ester by reaction with methanol saturated with dry HCl. The hydrochloride of the methyl ester of 3-phenyl-5-(2-carbomethoxyphenyl)pyrazole so obtained melts at 192°–4° C.

Reduction of the methyl ester with LiAlH$_4$ in tetrahydrofuran at the reflux temperature affords 3-phenyl-5-(2-hydroxymethylphenyl)-pyrazole which melts at 151°–3° C. after crystallization from isopropyl ether.

What is claimed is:

1. A tricyclic compound of the formula

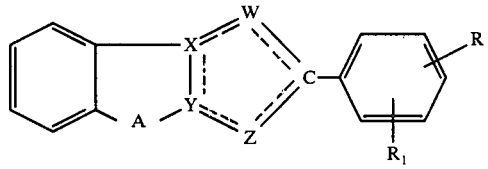

wherein:

A represents one of the groups —CH$_2$—; —CH═CH—; and —CH$_2$—CH$_2$—;

R represents one member of the group: hydrogen, lower alkyl, lower alkoxy, lower alkenyloxy, lower alkylnyloxy, cyclopropyloxy, cyclobutyloxy, cyclopentyloxy, cyclohexyloxy, hydroxy, benzyloxy, fluoro, chloro, bromo, iodo, trifluoromethyl and nitro; R$_1$ represents hydrogen, lower alkoxy, fluoro, chloro or bromo; or R and R$_1$ taken together represent a methylenedioxy group;

the sequence

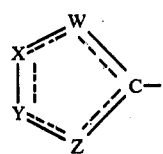

represents one of the following moieties:

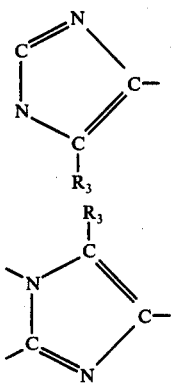

$R_3$ represents hydrogen or lower alkyl;
when the sequence

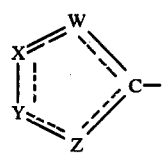

represents the moiety c) wherein $R_3$ is hydrogen and simultaneously both R and $R_1$ represent hydrogen, the symbol A may not represent the group —CH=CH—; and when the sequence

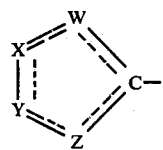

represents the moiety (d) wherein $R_3$ is hydrogen and simultaneously both R and $R_1$ represent hydrogen, the symbol A may not represent —CH=CH— or —CH$_2$—CH$_2$—; or a salt thereof with a non-toxic pharmaceutically-acceptable acid.

2. A compound as claimed in claim 1 wherein the sequence

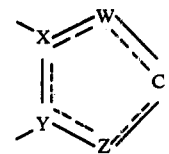

has one of the following structures:

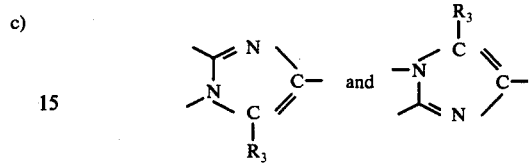

c)                d)

wherein $R_3$ is hydrogen or lower alkyl; A is one of —CH$_2$—CH$_2$— and —CH=CH—; wherein R and $R_1$ have the meanings given in claim 1 provided that at least one of R and $R_1$ is different from hydrogen.

3. A compound as claimed in claim 1 wherein the sequence

has the following structure:

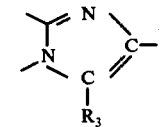

wherein $R_3$ is hydrogen, A is one of —CH=CH— and —CH$_2$—CH$_2$; R is located in position 3 or 4 of the phenyl radical and is one of the following: lower alkoxy, lower alkenyloxy, lower alkynyloxy, cyclopropyloxy, cyclobutyloxy, cyclopentyloxy, cyclohexyloxy, hydroxy, benzyloxy, fluoro, chloro and bromo; and $R_1$ is hydrogen or, taken together with R, represents methylenedioxy.

4. The compound as claimed in claim 1 which is 2-(4-chlorophenyl)imidazo[2,1-a]isoquinoline.

5. The compound as claimed in claim 1 which is 2-(4-bromophenyl)imidazo[2,1-a]isoquinoline.

6. A pharmaceutical composition having antireproductive activity containing as an active ingredient an effective amount of a compound as claimed in claim 1 together with a pharmaceutical carrier.

* * * * *

UNITED STATES PATENT AND TRADEMARK OFFICE
CERTIFICATE OF CORRECTION

PATENT NO. : 4,075,342
DATED : February 21, 1978
INVENTOR(S) : Amedeo Omodei Sale, et al.

It is certified that error appears in the above-identified patent and that said Letters Patent are hereby corrected as shown below:

First page, item 57 under Abstract, "notro" should read --nitro--;

First page, second column, --Formula d)-- should read

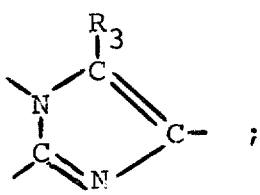

First page, second column, --Formula e)-- should read

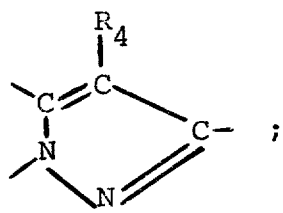

Column 1, line 20, "-CH=." should read ---CH=--;

Column 1, --Formula d)-- should read

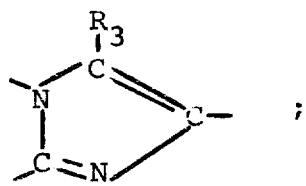

UNITED STATES PATENT AND TRADEMARK OFFICE
CERTIFICATE OF CORRECTION

PATENT NO. : 4,075,342
DATED : February 21, 1978
INVENTOR(S) : Amedeo Omodei Sale, et al.

It is certified that error appears in the above-identified patent and that said Letters Patent are hereby corrected as shown below:

Column 2, --Formula e)-- should read

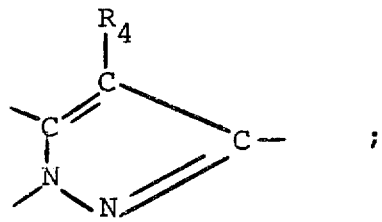

;

Column 3, line 1 "2butenyloxy" should read --2-butenyloxy--;

Column 3, line 8 "2-pentymyloxy" should read --2-pentynyloxy--;

Column 3, between lines 50 and 55, --Formula-- should read

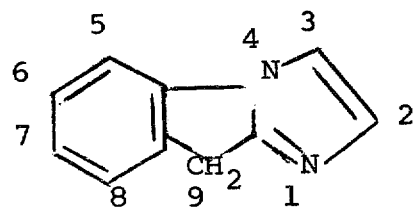

UNITED STATES PATENT AND TRADEMARK OFFICE
CERTIFICATE OF CORRECTION

PATENT NO. : 4,075,342

DATED : February 21, 1978

INVENTOR(S) : Amedeo Omodei Sale, et al.

It is certified that error appears in the above-identified patent and that said Letters Patent are hereby corrected as shown below:

Column 4, line 67 --"those compounds wherein the sequence has the following structure"-- should read --those compounds wherein the sequence 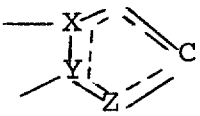 has the following structure Column 5, line 5 --omit Formula--.

Column 5, line 45 --"naphth[1,2-d]-imidazoles, i.e., compounds for formula I"-- should read --naphth[1,2-d]-imidazoles, i.e., compounds of formula I--;

Column 5, line 56 --"--$CH_2$--or--$CH_2$--$CH_2$--, a cyclic β-haloketone of--should read --$CH_2$ -or- $CH_2$ -$CH_2$ -, a cyclic α-haloketone of--;

UNITED STATES PATENT AND TRADEMARK OFFICE
CERTIFICATE OF CORRECTION

PATENT NO. : 4,075,342

DATED : February 21, 1978

INVENTOR(S) : Amedeo Omodei Sale, et al.

It is certified that error appears in the above-identified patent and that said Letters Patent are hereby corrected as shown below:

Column 8, line 21 "corresponding 5,6-dihydro-imidazo[1,2-a]isoquinoline," should read --corresponding 5,6-dihydro-imidazo[2,1-a]isoquinoline,--;

Column 10, line 62 "it may be transformed thrugh hydrogenolysis into the" should read --it may be transformed through hydrogenolysis into the--;

Column 12, line 4 "sponses to some of the highly effective anti-fertility" should read --sponses of some of the highly effective anti-fertility--;

Column 12, Table I, first line of Table "2-(4-chlorophenyl)imidazo- 0.25(s.d.)" should read --2-(4-chlorophenyl)imidazo - 0.25(s.c.)--;

Column 12, line 30 "The compounds may be administered by various" should read --The compounds of the invention may be administered by various--;

UNITED STATES PATENT AND TRADEMARK OFFICE
CERTIFICATE OF CORRECTION

PATENT NO. : 4,075,342
DATED : February 21, 1978
INVENTOR(S) : Amedeo Omodei Sale, et al.

It is certified that error appears in the above-identified patent and that said Letters Patent are hereby corrected as shown below:

Column 13, line 30 "(2.46 g.) dissolved in 10ml. of dimethylforamide, 0.5g." should read --(2.46g.) dissolved in 10ml. of dimethylformamide, 0.5g.--

Column 13, line 46 "indeno[1,2-d]-imidazole, 3-methyl-2-phenyl-8-" should read --indeno[1,2-d]-imidazole, 3-methyl-2-phenyl-8H- --;

Column 14, line 4 "85° under an argon atmosphere. Yiel 1.85g. of the" should read --85° under an argon atmosphere. Yield 1.85g. of the--;

Column 14, line 11 "tetophenone (16.35g.) in 30 ml. of $CHCL_3$ is added." should read --etophenone (16.35g.) in 30 ml. of $CHCL_3$ is added.--;

Column 14, line 52 "(15)  2(3,4-dichlorophenyl) imidazo [2,1-a] isoquinoline" should read --(15)  2-(3,4-dichlorophenyl)imidazo [2,1,-a] isoquinoline--;

UNITED STATES PATENT AND TRADEMARK OFFICE
CERTIFICATE OF CORRECTION

PATENT NO. : 4,075,342

DATED : February 21, 1978

INVENTOR(S) : Amedeo Omodei Sale, et al.

It is certified that error appears in the above-identified patent and that said Letters Patent are hereby corrected as shown below:

Column 15, line 45 "2(3-Allyloxyphenyl) imidazo[2,1-a]isoquinoline" should read --2-(3-Allyloxyphenyl)imidazo[2,1-a] isoquinoline--;

Column 17, line 1 "and the residue is washed with water and aqueous solu-" should read --and the residue is washed with water and acqueous sodium--;

Column 17, line 2 "tion carbonate. The resulting solid is extracted with" should read --carbonate. The resulting solid is extracted with--;

Column 17, line 23 "p-toluensulfonate (1.58g.) are refluxed for 3 hours in" should read --p-toluenesulfonate (1.58 g.) are refluxed for 3 hours in--;

Column 17, line 37 "melts at $190^0$C. with decompositon after crystallization" should read --melts at $190^0$C. with decomposition after crystallization--;

UNITED STATES PATENT AND TRADEMARK OFFICE
CERTIFICATE OF CORRECTION

PATENT NO. : 4,075,342
DATED : February 21, 1978
INVENTOR(S) : Amedeo Omodei Sale, et al.

It is certified that error appears in the above-identified patent and that said Letters Patent are hereby corrected as shown below:

Column 17, line 43 "2-Phenyl-5,6-dihydro-pyrazole[5,1-a]isoquinoline-1-" should read --(33) 2-Phenyl-5,6-dihydro-pyrazole [5,1-a]isoquinoline-1- --;

Column 20, line 8 "dry hydrogenbromide is maintained at 20°C. for 21" should read --dry hydrogen bromide is maintained at 20°C. for 21--;

Signed and Sealed this

Fourteenth Day of November 1978

[SEAL]

Attest:

RUTH C. MASON
Attesting Officer

DONALD W. BANNER
Commissioner of Patents and Trademarks